US012369998B2

(12) United States Patent
Tobergte et al.

(10) Patent No.: US 12,369,998 B2
(45) Date of Patent: Jul. 29, 2025

(54) REAL TIME MONITORING OF A ROBOTIC DRIVE MODULE (71) Applicant: Covidien LP, Mansfield, MA (US)

(72) Inventors: Andreas Tobergte, Munich (DE); Tom Baker, Germering (DE)

(73) Assignee: Covidien LP, Mansfield, MA (US)

( * ) Notice: Subject to any disclaimer, the term of this patent is extended or adjusted under 35 U.S.C. 154(b) by 555 days.

(21) Appl. No.: 17/737,256

(22) Filed: May 5, 2022

(65) Prior Publication Data
US 2022/0378523 A1 Dec. 1, 2022

Related U.S. Application Data (60) Provisional application No. 63/194,270, filed on May 28, 2021.

(51) Int. Cl.
A61B 34/30 (2016.01)
A61B 90/00 (2016.01)
B25J 9/16 (2006.01)
G16H 40/40 (2018.01)
G16H 40/63 (2018.01)

(52) U.S. Cl.
CPC ............ A61B 34/30 (2016.02); B25J 9/1674 (2013.01); G16H 40/40 (2018.01); G16H 40/63 (2018.01); A61B 2090/066 (2016.02)

(58) Field of Classification Search
CPC ............ A61B 34/30; A61B 2090/066; A61B 2017/00119; A61B 2017/00123; A61B 34/37; A61B 90/06; A61B 34/70; A61B 90/08; A61B 90/361; A61B 90/37; A61B 2034/306; A61B 2090/0807; B25J 9/1674; B25J 9/1689; G05B 2219/45118; G16H 40/40; G16H 40/63
See application file for complete search history.

(56) References Cited

U.S. PATENT DOCUMENTS

| 6,132,368 | A | 10/2000 | Cooper |
| 6,206,903 | B1 | 3/2001 | Ramans |
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |

(Continued)

FOREIGN PATENT DOCUMENTS

| WO | WO-2017169082 A1 | * | 10/2017 | ............. A61B 34/30 |
| WO | WO-2023246907 A1 | * | 12/2023 | |

OTHER PUBLICATIONS

WO-2023246907-A1 translation (Year: 2023).*

(Continued)

Primary Examiner — Kyle T Johnson
(74) Attorney, Agent, or Firm — Carter, DeLuca & Farrell LLP (57) ABSTRACT The surgical robotic system includes a robotic arm having one or more joints, each having a motor and at least one torque sensor and a velocity sensor. The system also includes a main controller, which outputs a drive command to the motor thereby actuating the motor. The system further includes a safety observer, which receives a measured velocity of the motor from the sensor, calculates an observed velocity, and detects a failure in operation of the at least one joint based on the observed velocity and the measured velocity.

17 Claims, 8 Drawing Sheets

(56) References Cited

U.S. PATENT DOCUMENTS

| | | |
|---|---|---|
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 * | 6/2010 | Prisco ............ B25J 9/1689 318/632 |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |

(56) References Cited

U.S. PATENT DOCUMENTS

| | | | |
|---|---|---|---|
| 8,858,547 | B2 | 10/2014 | Brogna |
| 8,862,268 | B2 | 10/2014 | Robinson et al. |
| 8,864,751 | B2 | 10/2014 | Prisco et al. |
| 8,864,752 | B2 | 10/2014 | Diolaiti et al. |
| 8,903,546 | B2 | 12/2014 | Diolaiti et al. |
| 8,903,549 | B2 | 12/2014 | Itkowitz et al. |
| 8,911,428 | B2 | 12/2014 | Cooper et al. |
| 8,912,746 | B2 | 12/2014 | Reid et al. |
| 8,944,070 | B2 | 2/2015 | Guthart |
| 8,989,903 | B2 | 3/2015 | Weir et al. |
| 9,002,518 | B2 | 4/2015 | Manzo |
| 9,014,856 | B2 | 4/2015 | Manzo et al. |
| 9,016,540 | B2 | 4/2015 | Whitman et al. |
| 9,019,345 | B2 | 4/2015 | O'Grady et al. |
| 9,043,027 | B2 | 5/2015 | Durant et al. |
| 9,050,120 | B2 | 6/2015 | Swarup et al. |
| 9,055,961 | B2 | 6/2015 | Manzo et al. |
| 9,068,628 | B2 | 6/2015 | Solomon et al. |
| 9,078,684 | B2 | 7/2015 | Williams |
| 9,084,623 | B2 | 7/2015 | Gomez et al. |
| 9,095,362 | B2 | 8/2015 | Dachs, II et al. |
| 9,096,033 | B2 | 8/2015 | Holop et al. |
| 9,101,381 | B2 | 8/2015 | Burbank et al. |
| 9,113,877 | B1 | 8/2015 | Whitman et al. |
| 9,138,284 | B2 | 9/2015 | Krom et al. |
| 9,144,456 | B2 | 9/2015 | Rosa et al. |
| 9,198,730 | B2 | 12/2015 | Prisco et al. |
| 9,204,923 | B2 | 12/2015 | Manzo et al. |
| 9,226,648 | B2 | 1/2016 | Saadat et al. |
| 9,226,750 | B2 | 1/2016 | Weir et al. |
| 9,226,761 | B2 | 1/2016 | Burbank |
| 9,232,984 | B2 | 1/2016 | Guthart et al. |
| 9,241,766 | B2 | 1/2016 | Duque et al. |
| 9,241,767 | B2 | 1/2016 | Prisco et al. |
| 9,241,769 | B2 | 1/2016 | Larkin et al. |
| 9,259,275 | B2 | 2/2016 | Burbank |
| 9,259,277 | B2 | 2/2016 | Rogers et al. |
| 9,259,281 | B2 | 2/2016 | Griffiths et al. |
| 9,259,282 | B2 | 2/2016 | Azizian et al. |
| 9,261,172 | B2 | 2/2016 | Solomon et al. |
| 9,265,567 | B2 | 2/2016 | Orban, III et al. |
| 9,265,584 | B2 | 2/2016 | Tkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,533 | B2 | 11/2016 | Devengenzo et al. |
| 9,503,713 | B2 | 11/2016 | Zhao et al. |
| 9,550,300 | B2 | 1/2017 | Danitz et al. |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,675,354 | B2 | 6/2017 | Weir et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,044 | B2 | 5/2018 | Gomez et al. |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,344 | B2 | 10/2018 | Mohr et al. |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,335,242 | B2 | 7/2019 | Devengenzo et al. |
| 10,405,934 | B2 | 9/2019 | Prisco et al. |
| 10,433,922 | B2 | 10/2019 | Itkowitz et al. |
| 10,464,219 | B2 | 11/2019 | Robinson et al. |
| 10,485,621 | B2 | 11/2019 | Morrissette et al. |
| 10,500,004 | B2 | 12/2019 | Hanuschik et al. |
| 10,500,005 | B2 | 12/2019 | Weir et al. |
| 10,500,007 | B2 | 12/2019 | Richmond et al. |
| 10,507,066 | B2 | 12/2019 | DiMaio et al. |
| 10,510,267 | B2 | 12/2019 | Jarc et al. |
| 10,524,871 | B2 | 1/2020 | Liao |
| 10,548,459 | B2 | 2/2020 | Itkowitz et al. |
| 10,575,909 | B2 | 3/2020 | Robinson et al. |
| 10,592,529 | B2 | 3/2020 | Hoffman et al. |
| 10,595,946 | B2 | 3/2020 | Nixon |
| 10,881,469 | B2 | 1/2021 | Robinson |
| 10,881,473 | B2 | 1/2021 | Itkowitz et al. |
| 10,898,188 | B2 | 1/2021 | Burbank |
| 10,898,189 | B2 | 1/2021 | McDonald, II |
| 10,905,506 | B2 | 2/2021 | Itkowitz et al. |
| 10,912,544 | B2 | 2/2021 | Brisson et al. |
| 10,912,619 | B2 | 2/2021 | Jarc et al. |
| 10,918,387 | B2 | 2/2021 | Duque et al. |
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 10,939,969 | B2 | 3/2021 | Swarup et al. |
| 10,939,973 | B2 | 3/2021 | DiMaio et al. |
| 10,952,801 | B2 | 3/2021 | Miller et al. |
| 10,965,933 | B2 | 3/2021 | Jarc |
| 10,966,742 | B2 | 4/2021 | Rosa et al. |
| 10,973,517 | B2 | 4/2021 | Wixey |
| 10,973,519 | B2 | 4/2021 | Weir et al. |
| 10,984,567 | B2 | 4/2021 | Itkowitz et al. |
| 10,993,773 | B2 | 5/2021 | Cooper et al. |
| 10,993,775 | B2 | 5/2021 | Cooper et al. |
| 11,000,331 | B2 | 5/2021 | Krom et al. |

(56) References Cited

U.S. PATENT DOCUMENTS

| | | |
|---|---|---|
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2008/0255772 A1* | 10/2008 | Sjostrand ............... B25J 9/1674 702/34 |
| 2012/0010748 A1* | 1/2012 | Sasai .................... G01C 25/005 700/254 |
| 2012/0089254 A1* | 4/2012 | Shafer ...................... B25J 17/00 901/46 |
| 2017/0007336 A1* | 1/2017 | Tsuboi ................... B25J 9/1674 |
| 2019/0143513 A1* | 5/2019 | Rabindran ............. B25J 9/1607 700/245 |
| 2020/0171661 A1* | 6/2020 | Kinugasa ............... B25J 9/1628 |
| 2020/0324419 A1* | 10/2020 | Kuroda ............... A61B 1/00149 |
| 2022/0378523 A1* | 12/2022 | Tobergte ................ B25J 9/1689 |
| 2023/0063521 A1* | 3/2023 | Yu .......................... A61B 34/37 |

OTHER PUBLICATIONS

WO-2017169082-A1 translation (Year: 2017).*
Design_of_a_joint_angle_measurement_system2019.pdf (Year: 2019).*
Torque_Estimation_for_Robotic_Joint_With_Harmonic_Drive_Transmission (Year: 2015).*

* cited by examiner

REAL TIME MONITORING OF A ROBOTIC DRIVE MODULE

CROSS-REFERENCE TO RELATED APPLICATION

This application claims the benefit of and priority to U.S. Patent Provisional Application No. 63/194,270, filed on May 28, 2021. The entire disclosure of the foregoing application is incorporated by reference herein.

BACKGROUND

Technical Field

The present disclosure generally relates to surgical robotic systems and in particular to drive modules, i.e., actuators, configured to move various components of surgical robotic arms. More specifically, the present disclosure relates to a system and method for real-time monitoring of the robotic drive modules to detect failures.

Background of Related Art

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body. Operation the robotic arm may be continuously monitored during its operation to detect failure of various components of the robotic arm, such as its actuators.

SUMMARY

According to one embodiment of the present disclosure, a surgical robotic system is disclosed. The surgical robotic system includes a robotic arm including at least one joint having a motor and at least one sensor. The system also includes a main controller configured to output a drive command, i.e., torque command, to the motor to actuate the motor. The system further includes a safety observer configured to: receive a measured velocity from the sensor, calculate an observed velocity, and detect a failure in operation of the at least one joint based on the observed velocity and the measured velocity.

Implementations of the above embodiment may include one or more of the following features. According to one aspect of the above embodiment, the safety observer is further configured to output an error to the main controller in response to detection of the failure. One or more of the sensors may include a joint torque sensor configured to measure joint torque of the at least one joint. One or more of the sensors may further include a motor sensor configured to measure motor torque of the motor. The safety observer may be further configured to calculate the observed velocity based on the joint torque and the motor torque. The safety observer may be further configured to calculate a velocity difference between the observed velocity and the measured velocity. The safety observer may be further configured to compare the velocity difference to a velocity error range. The safety observer may be further configured to detect the failure in response to the velocity difference being outside the velocity error range.

According to another embodiment of the present disclosure, a method for controlling a surgical robot is disclosed. The method includes outputting a drive command at a main controller to a motor of at least one joint of a robotic arm to actuate the motor. The method also includes measuring velocity of the motor using at least one sensor and receiving at a safety observer a measured velocity from the at least one sensor. The method also includes calculating at the safety observer an observed velocity and detecting at a safety observer a failure in operation of the at least one joint based on the observed velocity and the measured velocity.

Implementations of the above embodiment may include one or more of the following features. According to one aspect of the above embodiment, the method may further include: measuring joint torque of the at least one joint at a joint torque sensor; and measuring motor torque of the motor at a motor sensor. The method may also include: calculating the observed velocity based on the joint torque and the motor torque; and calculating a velocity difference between the observed velocity and the measured velocity. The method may further include: comparing the velocity difference to a velocity error range; and detecting the failure in response to the velocity difference being outside the velocity error range.

According to a further embodiment of the present disclosure, a surgical robotic system is disclosed. The surgical robotic system includes a robotic arm including at least one joint having a motor and at least one torque sensor and a velocity sensor. The system also includes a main controller configured to output a drive command to the motor to actuate the motor. The system further includes a safety observer configured to receive a measured velocity from the velocity sensor and at least one torque measurement from the at least one torque sensor; calculate an observed velocity based on the at least one torque measurement; and detect a failure in operation of the at least one joint based on the observed velocity and the measured velocity.

Implementations of the above embodiment may include one or more of the following features. According to one aspect of the above embodiment, the safety observer is further configured to output an error to the main controller in response to detection of the failure. One or more of the torque sensors may include a joint torque sensor configured to measure joint torque of the at least one joint. One or more of the torque sensors may include a motor sensor configured to measure motor torque of the motor. The safety observer is further configured to calculate the observed velocity based on the joint torque and the motor torque. The safety observer is further configured to calculate a velocity difference between the observed velocity and the measured velocity. The safety observer is further configured to compare the velocity difference to a velocity error range. The safety observer is further configured to detect the failure in response to the velocity difference being outside the velocity error range.

BRIEF DESCRIPTION OF THE DRAWINGS

Various embodiments of the present disclosure are described herein with reference to the drawings wherein.

DETAILED DESCRIPTION

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, a personal computer, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

Figure 1:
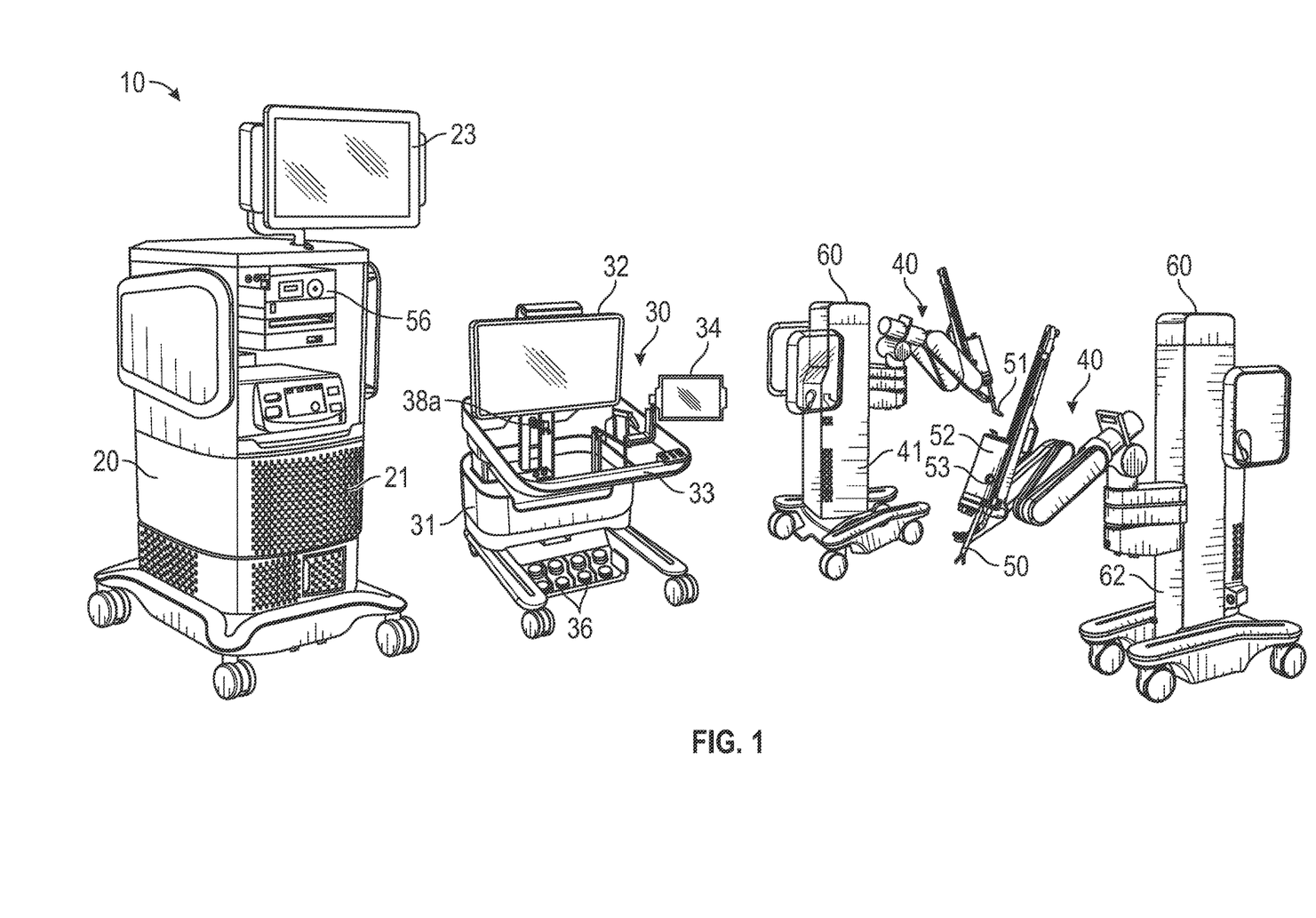
FIG. 1 is a schematic illustration of a surgical robotic system including a control tower, a console, and one or more surgical robotic arms according to an embodiment of the present disclosure.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include the endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 perform the image processing based on the depth estimating algorithms of the present disclosure and output the processed video stream.

The surgical console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgical console 30 also includes a plurality of user interface devices, such as foot pedals 36 and a pair of handle controllers 38a and 38b which are used by a user to remotely control robotic arms 40. The surgical console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, BLUETOOTH® (an open wireless protocol for exchanging data over short distances, using short length radio waves, from fixed and mobile devices, creating personal area networks (PANs)), ZIGBEE® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
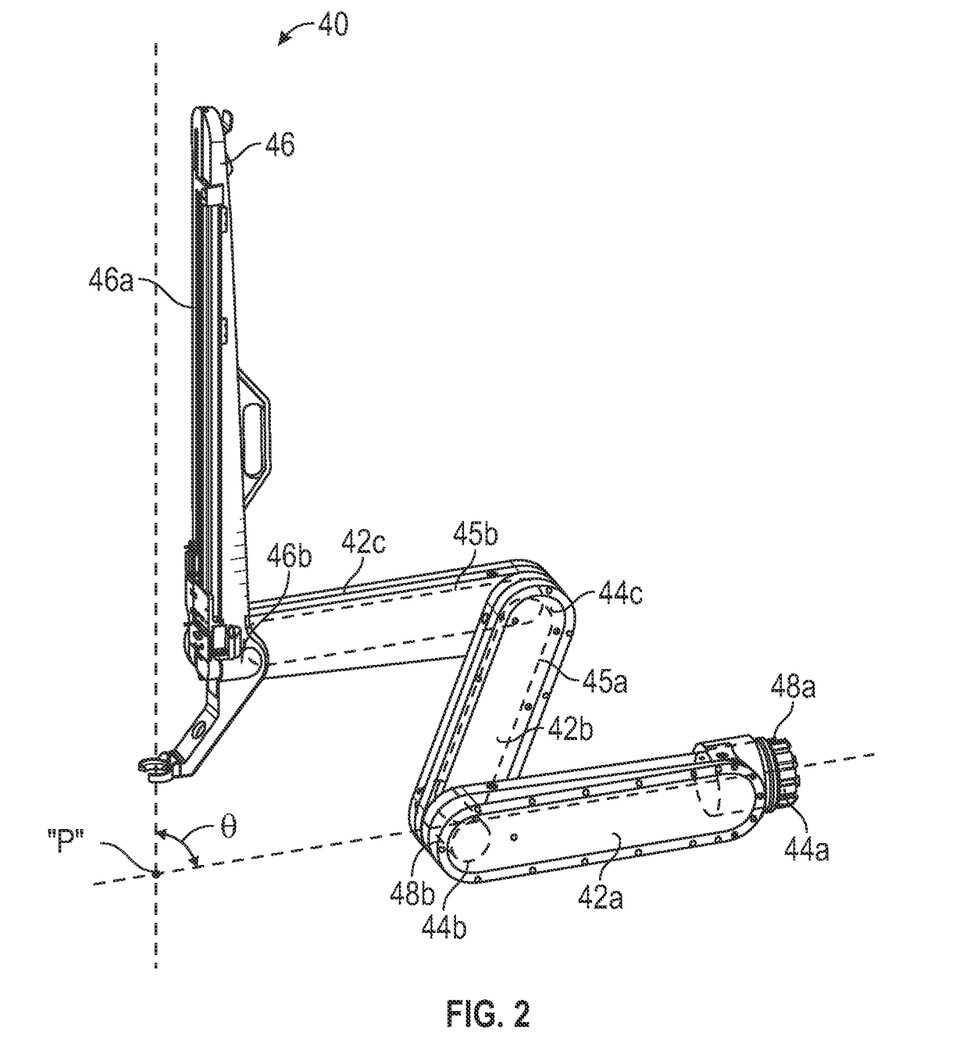
FIG. 2 is a perspective view of a surgical robotic arm of the surgical robotic system of FIG. 1 according to an embodiment of the present disclosure.
Figure 3:
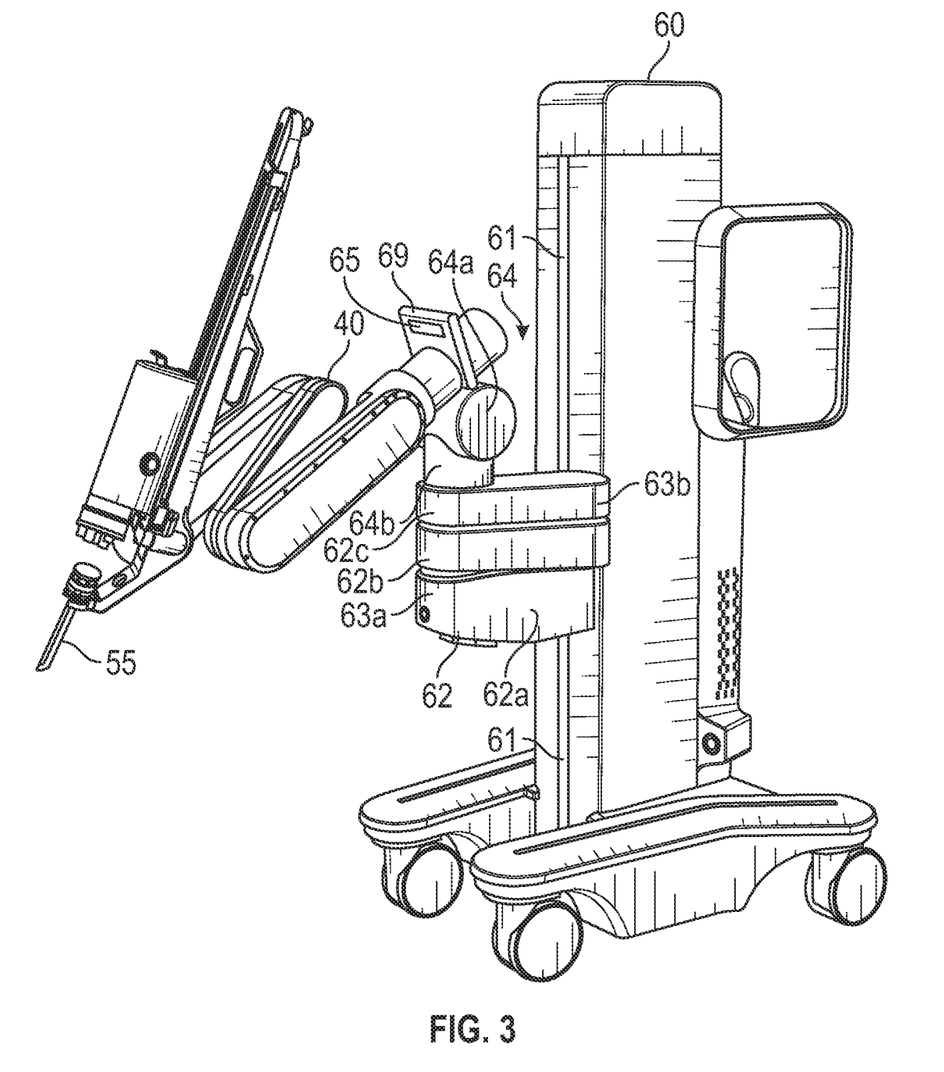
FIG. 3 is a perspective view of a setup arm with the surgical robotic arm of the surgical robotic system of FIG. 1 according to an embodiment of the present disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c. During endoscopic procedures, the instrument 50 may be inserted through an endoscopic port 55 (FIG. 3) held by the holder 46.

The robotic arm 40 also includes a plurality of manual override buttons 53 (FIGS. 1 and 5) disposed on the IDU 52 and the setup arm 62, which may be used in a manual mode. The user may press one or more of the buttons 53 to move the component associated with the button 53.

Figure 4:
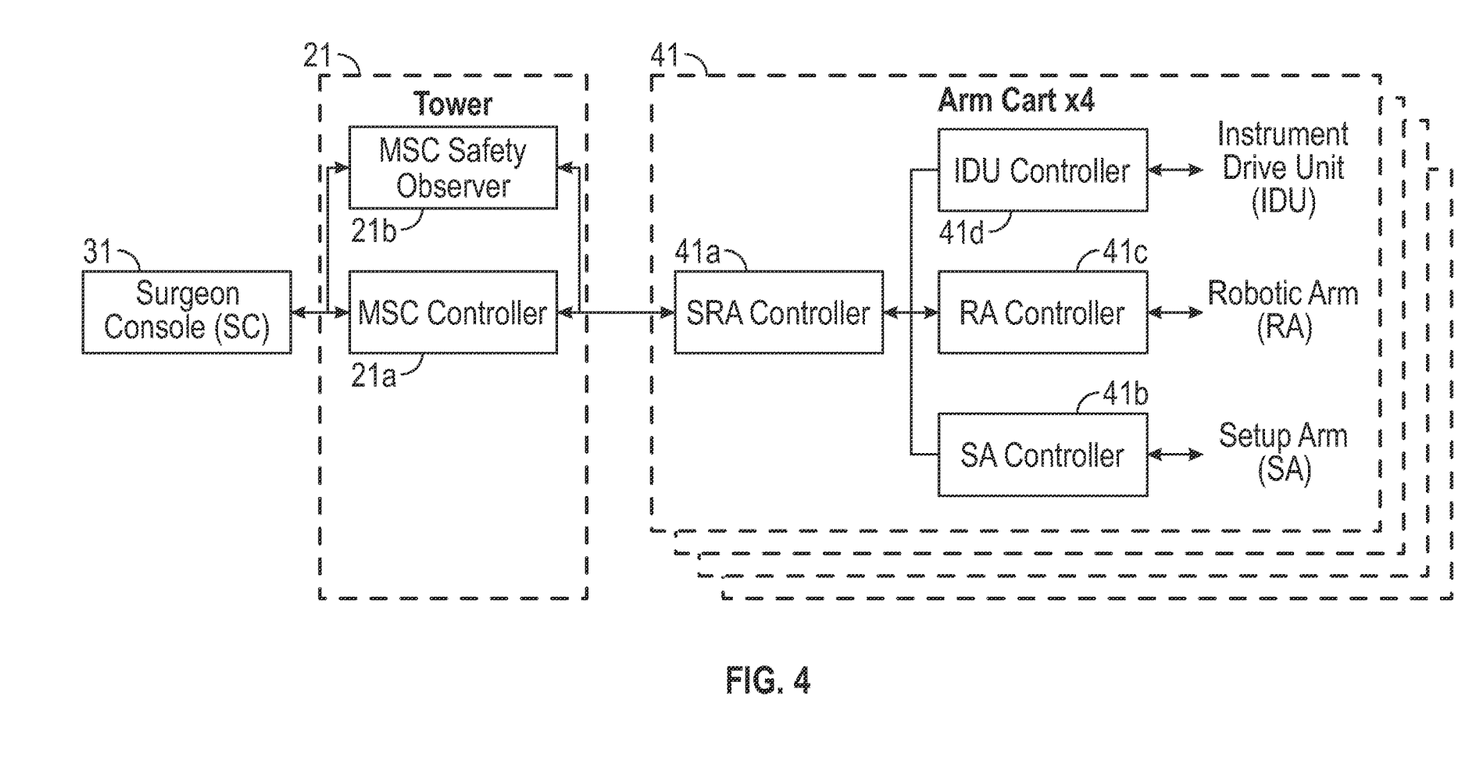
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a main controller 21a and a safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives the actual joint angles measured by encoders of the actuators 48a and 48b and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state. In embodiments, the safety observer 21b may be embodied as software executable by the controller 21a rather than being a separate controller.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the IDU 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled in response to a pose of the handle controller controlling the robotic arm 40, e.g., the handle controller 38a, which is transformed into a desired pose of the robotic arm 40 through a hand eye transform function executed by the controller 21a. The hand eye function, as well as other functions are embodied in software executable by the controller 21a or any other suitable controller described herein. The pose of one of the handle controller 38a may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38a is then scaled by a scaling function executed by the controller 21a. In embodiments, the coordinate position is scaled down and the orientation is scaled up by the scaling function. In addition, the controller 21a also executes a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

The robotic arm controller 41c is also configured to estimate torque imparted on the joints 44a and 44b by the rigid link structure of the robotic arm 40, namely, the links 42a, 42b, 42c. Each of the joints 44a and 44b houses actuator 48a and 48b. High torque may be used to move the robotic arm 40 due to the heavy weight of the robotic arm 40. However, the torque may need to be adjusted to prevent damage or injury. This is particularly useful for limiting torque during collisions of the robotic arm 40 with external objects, such as other robotic arms, patient, staff, operating room equipment, etc.

In order to determine the effect of external torque on the robotic arm 40 the robotic arm controller 41c initially calculates frictional losses, gravitational forces, inertia, and then determines the effects of external torque. Once the external torque is calculated, the robotic arm controller 41c determines whether the environmental forces exceed a predetermined threshold which is indicative of collisions with external objects and takes precautionary action, such as terminating movement in the direction in which collision was detected, slowing down, and/or reversing movement (e.g., moving in an opposite direction) for a predetermined distance.

Figure 5:
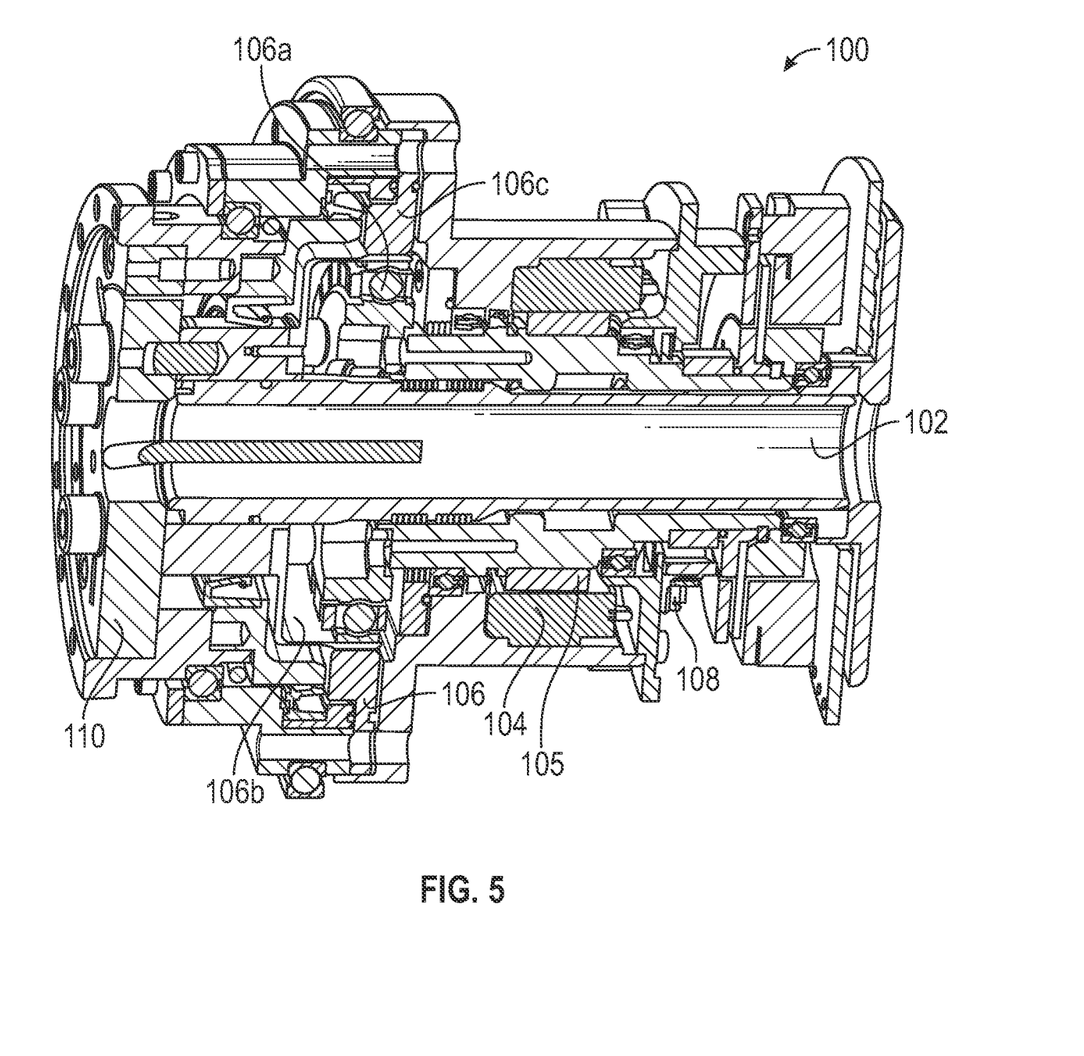
FIG. 5 is a cross-sectional view of an actuator of the surgical robotic arm of FIG. 2 according to the present disclosure.

The sensor measurements and calculations based thereon are described below with respect to FIG. 5, which shows an integrated joint module 100. The integrated joint module 100 may be used as the actuators 48a, 48b, 64a, 64b, and as the actuators within the joints 63a and 63b. The integrated joint module 100 includes a shaft 102, which acts as a support structure for the other components of the integrated joint module 100, namely, a motor 104 and a harmonic gearbox 106. The motor 104 may be any electric motor, which may be powered by AC or DC energy, such as a brushed motor, a brushless motor, a stepper motor, and the like. The motor 104 is coupled to the harmonic gearbox 106, which may be a harmonic drive gear configured to provide a large reduction ratio with approximately zero backlash, high torque capability, and high efficiency. The harmonic gearbox 106 may include concentric input and output shafts (not shown) and may include a wave generator 106a, disposed within a flexspline 106b having an outer geared surface, which is in turn, disposed within a circular spline 106c having an inner geared surface. As the motor 104 drives the wave generator 106a, the flexspline 106b, which may be formed from an elastic material, such as stainless steel, is also rotated. The flexspline 106b has fewer teeth than the circular spline 106c, therefore for every full rotation of the wave generator 106a, the flexspline 106b rotates less than a full rotation, which reduces the output speed. The harmonic gearbox 106 is in turn coupled to one of the belts 45a or 45b.

The integrated joint module 100 also includes a sensor suite for monitoring the performance of the integrated joint module 100 to provide for feedback and control thereof. In particular, the integrated joint module 100 includes an encoder 108 coupled to the motor 104. The encoder 108 may be any device that provides a sensor signal indicative of the number of rotations of the motor 104, such as a mechanical encoder or an optical encoder. The motor 104 may also include other sensors, such as a current sensor configured to measure the current draw of the motor 104, a motor torque sensor 105 for measuring motor torque, and the like. The number of rotations may be used to determine the speed and/or position control of individual joints 44a, 44b, 44c. Parameters which are measured and/or determined by the encoder 108 may include speed, distance, revolutions per minute, position, and the like. The integrated joint module 100 further includes a joint torque sensor 110 may be any force or strain sensor including one or more strain gauges configured to convert mechanical forces and/or strain into a sensor signal indicative of the torque imparted by the harmonic gearbox 106. The sensor signals from the encoder 108 and the joint torque sensor 110 are transmitted to the computer 41, which then controls the speed, angle, and/or position of each of the joints 44a, 44b, 44c of the robotic arm 40 based on the sensor signals. In embodiments, additional position sensors may also be used to determine movement and orientation of the robotic arm 40 and the setup arm 62. Suitable sensors include, but are not limited to, potentiometers coupled to movable components and configured to detect travel distances, Hall Effect sensors, accelerometers, and gyroscopes.

Figure 6:
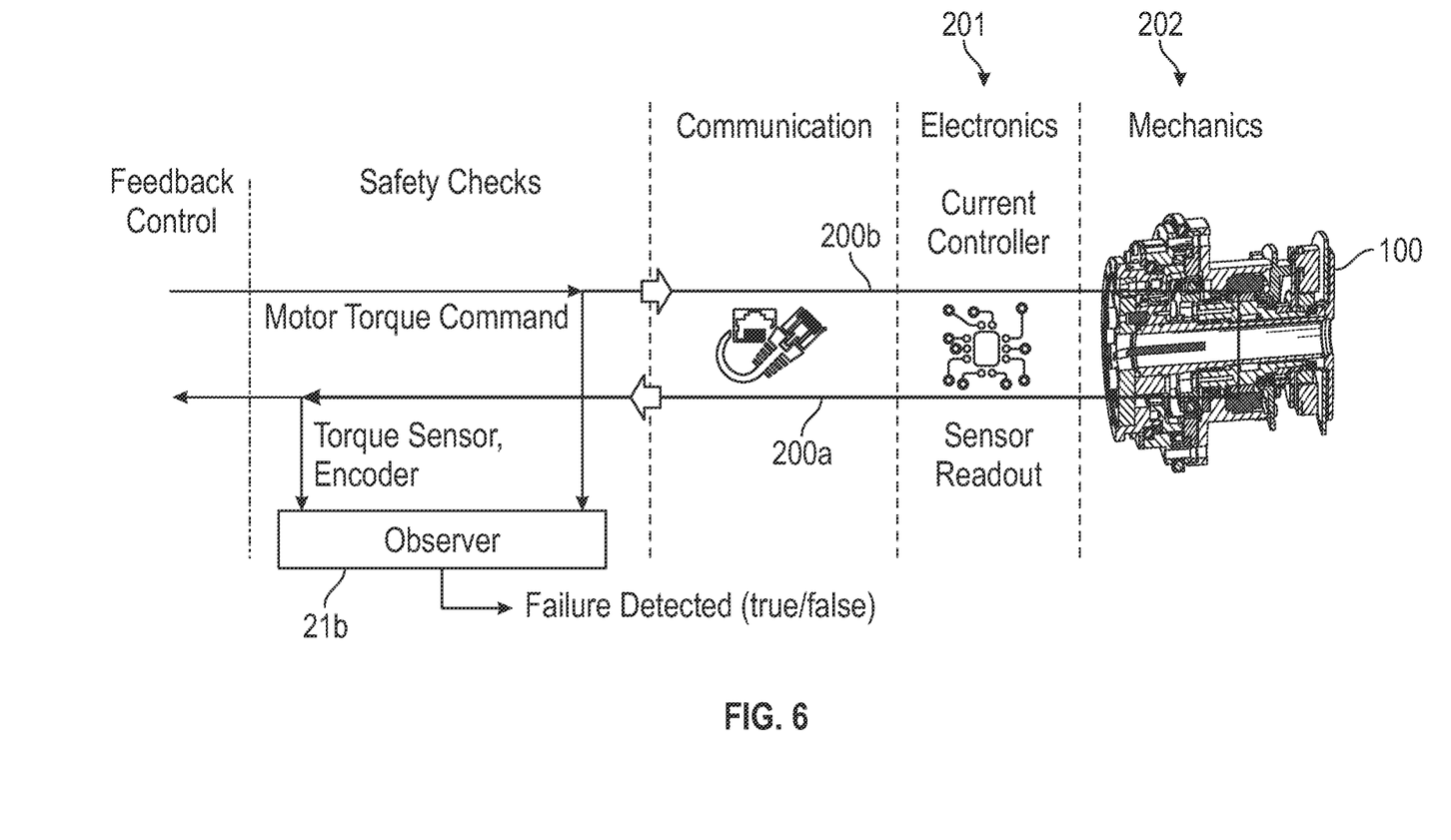
FIG. 6 is a schematic safety observer system according to the present disclosure.

With reference to FIG. 6, the safety observer 21b is shown as processing sensor signals from the integrated joint module 100. The integrated joint module 100 outputs sensor signals from electronic components 201 (e.g., current sensor) and mechanical components 202 (e.g., the motor torque sensor 105, the joint torque sensor 110, the encoder 108, etc.). Sensor signals are shown as an output 200a. The output 200a is provided over a wired (e.g., ETHERCAT® or any other Ethernet-based fieldbus system) or a wireless connection to the controller 21a. The controller 21a utilizes the output 200a to control the integrated joint module 100 as described above, e.g., transmitting drive commands to the integrated joint module 100, which in turn, achieves the commanded pose. The drive commands are shown as an input 200b.

The safety observer 21b compares the output 200a and the input 200b to determine if there is a failure, which includes a failure in communication, electronic components 201, mechanical components 202 (e.g., error in the torque sensor readings), the motor 104 (e.g., error in the applied torque), etc.

According to one embodiment, the safety observer 21b is configured to determine a failure by calculating a total torque error based on a difference between joint torque sensor measurement from the joint torque sensor 110 and commanded motor torque, which is based on the drive command from the controller 21a.

According to another embodiment, the safety observer 21b is configured to determine a failure by estimating velocity of the motor 104 from a drive train simulation. The estimated velocity is then compared with actual velocity of the motor 104 as measured by the encoder 108. The drive train model may be represented by formula (1) below:

$$\tau_{m,d} = b\ddot{\theta} + \tau_{fric}(\dot{\theta}, \tau_j) + \tau_j \qquad 1)$$

where $\tau_{m,d}$ is the commanded motor torque based on actuator input and may be measured based on the magnetic field generated by the motor 104, $\tau_m$, is the measured motor torque which is based on actuator output, b is inertia of the motor 104 and the harmonic gearbox 106, $\ddot{\theta}$ is the acceleration, $\tau_{fric}$ is the friction of the motor 104 and the harmonic gearbox 106, and $\tau_j$ is the joint torque based on actuator output and is measured using the joint torque sensor 110 representative of the mechanical strain. The observer may be implemented with $\tau_{m,d}$ or $\tau_m$.

In addition, $\tau_{fric}$, the friction of the motor 104 and the harmonic gearbox 106 may be represented by formula (2) below:

$$\tau_{fric}(\dot{\theta}, \tau_j) = (f_c + f_l|\tau_j|)\text{sign}(\dot{\theta}) + f_v\dot{\theta} \qquad 2)$$

Thus, $\tau_{fric}$ is a sum of Coulomb friction, represented as, $(f_c + f_l|\tau_j|)\text{sign}(\dot{\theta})$, which is based on direction of motion and is load dependent, and $f_v\dot{\theta}$, is a viscous friction, which is velocity dependent.

Based on the above formulas, the observer model is based on the drive train model but incorporates sensor errors into the formulas. Thus, the observer model may be represented by formula (3) below and the individual errors in formulas (4)-(6):

$$\tau_{m,d} = b\ddot{\theta} + \tau_{fric}(\dot{\theta}, \tau_j) + \tau_s + \tau_{error} \qquad 3)$$

$$\tau_{error} = \tau_{s,error} - \tau_{m,error} \qquad 4)$$

$$\tau_{m,d} = \tau_m + \tau_{m,error} \qquad 5)$$

$$\tau_s = \tau_j + \tau_{s,error} \qquad 6)$$

Thus, $\tau_{error}$ is a difference between joint torque error, $\tau_{s,error}$, and actuator input error, $\tau_{m,error}$. The observer model may be used to determine the observed (i.e., estimated) velocity using formula (7):

$$\dot{\theta}_{observed} = \int_{t_0}^{t} \frac{1}{b}[\tau_{m,d} - \tau_s - [(f_c + f_l|\tau_j|)\text{sign}(\dot{\theta}) + f_v\dot{\theta}]] \qquad 7)$$

Figure 7:
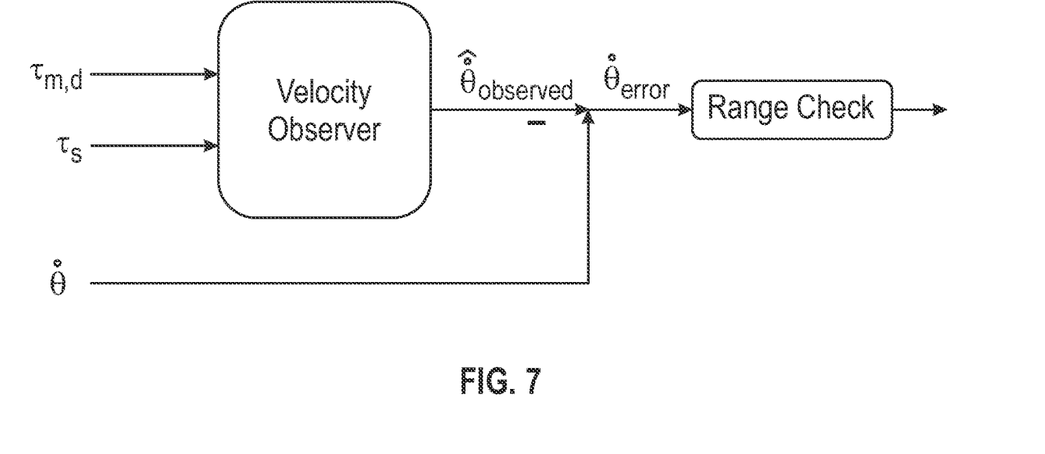
FIG. 7 is a flow chart of an algorithm implemented in a safety observer according to the present disclosure.

As shown in FIG. 7, which shows a flow chart of a method for determining velocity error, the velocity error is determined based on a difference of actual velocity and observed velocity (determined using the observer model). In particular, the velocity observer calculates observed velocity based on $\tau_{m,d}$ and $\tau_{sm}$. The velocity error may then also be compared to a range of velocity error limits to determine if the error is sufficient to issue an alarm and/or stop operation.

The present disclosure also provides for modifying the observer model implemented in the safety observer 21b to increase its bandwidth. In particular, the dynamics of the observer model are limited or equal to the drive train model, which is relatively slow, especially when viewed in the context of requirements for detecting velocity errors. Thus, the observer model may be updated to increase dynamics by reducing sensitivity to variation of mechanical viscous friction. This may be accomplished by accounting for kinetic friction, $f_k\dot{\theta}$, which is added to both sides of the observer model as shown in formula (8), which is based on formula (3) above.

$$\tau_{m,d} + f_k\dot{\theta} = b\ddot{\theta} + \tau_{fric}(\dot{\theta}, \tau_j) + f_k\dot{\theta} + \tau_s + \tau_{error} \qquad 8)$$

Similarly, observed velocity may be calculated using formula (9) below, which is based on formula (7) above:

$$\dot{\theta}_{observed} = \int_{t_0}^{t} \frac{1}{b}[\tau_{m,d} + f_k\dot{\theta} - \tau_s - [(f_c + f_l|\tau_j|)\text{sign}(\dot{\theta}) + f_v\dot{\theta} + f_k\dot{\theta}]] \qquad 9)$$

Figure 8:
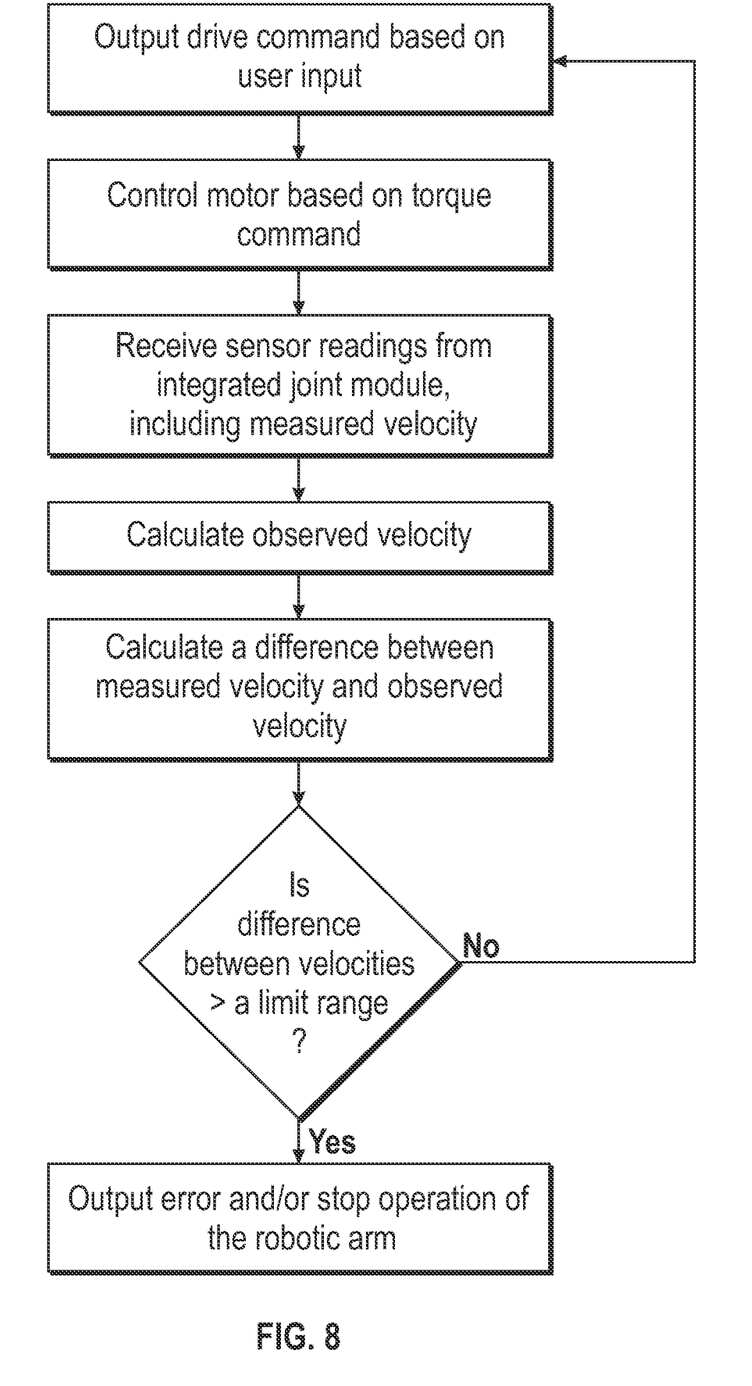
FIG. 8 is a flow chart of a method for detecting failure of an integrated joint module according to the present disclosure.

The method for detecting failures in the applied torque of the joint module 100 is described with reference to FIG. 8. A movement command from the handle controller 38a is output as a specific drive command by the controller 21a to the integrated joint module 100. The drive command instructs the motor 104 to output a specific torque to achieve the commanded movement. As the motor 104 is actuated, various sensors, e.g., current sensor, the motor torque sensor 105, the joint torque sensor 110, the encoder 108, etc. provide feedback including current, motor torque, sensor torque, and motor speed, to the controller 21a and the safety observer 21b. In particular, the safety observer 21b receives measured velocity of the motor 104.

The safety observer 21b also calculates observed velocity as described above, based on error-adjusted motor torque $\tau_{m,d}$ and error-adjusted joint torque $\tau_s$ (see FIG. 7). The safety observer 21b also calculates a difference between measured velocity and observed velocity. The difference is then compared to a range limit as shown in formula (10):

$$-\dot{\theta}_{limit} \leq \dot{\theta} - \dot{\theta}_{observed} \leq \dot{\theta}_{limit}$$

The positive and negative $\dot{\theta}_{limit}$ values represent error amounts indicative of a mismatch between measured and observed velocities due to a failure in applied torque of the integrated joint module 100 and/or torque sensor readings. Thus, if the velocity error is within the limit, the integrated joint module 100 may continue to operate. However, if the velocity error is outside the limit, the safety observer 21b outputs an error to the controller 21a which may handle the error according to any prescribed method, such as stop operation of the robotic arm 40 and/or output error on displays, etc.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
   a robotic arm including at least one joint having a motor;
   an encoder configured to measure motor velocity;
   a joint torque sensor configured to measure joint torque of the at least one joint;
   a motor torque sensor configured to measure motor torque;
   a safety observer configured to:
      receive a measured velocity of the motor from the encoder;
      calculate an observed velocity of the motor based on the joint torque and the motor torque; and
      detect a failure in operation of the at least one joint based on a velocity difference between the calculated observed velocity and the measured velocity; and
   a main controller configured to output a drive command to the motor to actuate the motor and to stop the motor in response to detection of the failure.

2. The surgical robotic system according to claim 1, wherein the safety observer is further configured to output an error to the main controller in response to detection of the failure.

3. The surgical robotic system according to claim 1, wherein the safety observer is further configured to:
   compare the velocity difference to a velocity error range.

4. The surgical robotic system according to claim 3, wherein the safety observer is further configured to detect the failure in response to the velocity difference being outside the velocity error range.

5. The surgical robotic system according to claim 1, wherein the safety observer is further configured to calculate the observed velocity based on the joint torque and commanded motor torque of the drive command.

6. A surgical robotic system comprising:
   a robotic arm including at least one joint having a motor and at least one torque sensor and a velocity sensor;
   a safety observer configured to:
      receive a measured velocity of the motor from the velocity sensor and at least one torque measurement from the at least one torque sensor;
      calculate an observed velocity of the motor based on the at least one torque measurement; and
      detect a failure in operation of the at least one joint based on a velocity difference between the calculated observed velocity and the measured velocity; and
   a main controller configured to output a drive command to the motor to actuate the motor and to stop the motor in response to detection of the failure.

7. The surgical robotic system according to claim 6, wherein the safety observer is further configured to output an error to the main controller in response to detection of the failure.

8. The surgical robotic system according to claim 6, wherein the at least one torque sensor includes a joint torque sensor configured to measure joint torque of the at least one joint.

9. The surgical robotic system according to claim 8, wherein the at least one torque sensor further includes at least one motor sensor configured to measure a motor torque of the motor.

10. The surgical robotic system according to claim 9, wherein the safety observer is further configured to calculate the observed velocity based on the joint torque and the motor torque.

11. The surgical robotic system according to claim 10, wherein the safety observer is further configured to:
    compare the velocity difference to a velocity error range.

12. The surgical robotic system according to claim 11, wherein the safety observer is further configured to detect the failure in response to the velocity difference being outside the velocity error range.

13. The surgical robotic system according to claim 8, wherein the safety observer is further configured to calculate the observed velocity based on the joint torque and commanded motor torque of the drive command.

14. A method for controlling a surgical robot, the method comprising:
    outputting a drive command at a main controller to a motor of at least one joint of a robotic arm to actuate the motor;
    measuring velocity of the motor using a velocity sensor;
    measuring motor torque of the motor using at least one motor sensor;
    receiving at a safety observer a measured velocity from the velocity sensor;
    calculating at the safety observer an observed velocity;
    detecting at the safety observer a failure in operation of the at least one joint based on a velocity difference between the calculated observed velocity and the measured velocity; and
    stopping the motor in response to detection of the failure.

15. The method according to claim 14, further comprising:
    measuring joint torque of the at least one joint at a joint torque sensor.

16. The method according to claim 15, further comprising:
    calculating the observed velocity based on the joint torque and the motor torque.

17. The method according to claim 16, further comprising:
    comparing the velocity difference to a velocity error range; and
    detecting the failure in response to the velocity difference being outside the velocity error range.

* * * * *